US006676287B1

(12) United States Patent
Mathis et al.

(10) Patent No.: US 6,676,287 B1
(45) Date of Patent: Jan. 13, 2004

(54) DIRECT THERMAL CONDUCTIVITY MEASUREMENT TECHNIQUE

(75) Inventors: Nancy Mathis, Fredericton (CA); Christina Chandler, San Jose, CA (US)

(73) Assignee: Mathis Instruments Ltd., Fredericton, CA (US)

( * ) Notice: Subject to any disclaimer, the term of this patent is extended or adjusted under 35 U.S.C. 154(b) by 0 days.

(21) Appl. No.: 10/213,662

(22) Filed: Aug. 7, 2002

(51) Int. Cl.⁷ .......................... G01N 25/18; G01K 15/00
(52) U.S. Cl. ................................ 374/1; 374/44
(58) Field of Search ............................. 374/1, 44, 10, 374/11, 31, 33

(56) References Cited

U.S. PATENT DOCUMENTS

| | | | | |
|---|---|---|---|---|
| 3,279,239 A | * | 10/1966 | Arends et al. | 374/44 |
| 3,733,887 A | * | 5/1973 | Stanley et al. | 374/44 |
| 3,971,246 A | | 7/1976 | Sumikama et al. | |
| 4,630,938 A | * | 12/1986 | Piorkowska-Palczewska et al. | 374/44 |
| 4,859,078 A | * | 8/1989 | Bowman et al. | 374/44 |
| 5,038,304 A | * | 8/1991 | Bonne | 702/99 |
| 5,112,136 A | * | 5/1992 | Sakuma et al. | 374/44 |
| 5,452,601 A | * | 9/1995 | Hori et al. | 73/54.42 |
| 5,795,064 A | | 8/1998 | Mathis | |
| 6,397,003 B1 | | 5/2002 | Cheng | |

FOREIGN PATENT DOCUMENTS

| JP | 57082755 A | * | 5/1982 | G01N/25/18 |
|---|---|---|---|---|
| JP | 60036944 A | * | 2/1985 | G01N/25/18 |

OTHER PUBLICATIONS

Review and Comparison of Thermal Conductivity Instruments; Nancy Mathis; Research, Product Development & Manufacturing, Mathis Instruments Ltd.; Aug. 20, 1998.
TC Probe ™ Test Technique: Inverse Blotter Method; Craig Dixon; Research, Product Development & Manufacturing, Mathis Instruments Ltd.; Nov. 23, 1998.
TC Probe ™ Workbook 3, A Comprehensive Guide for Quality control Testing of Vacuum Insulation Panels; Mathis Instruments Ltd.; Oct. 8, 1999.
TC Probe ™ Application: Pharmaceutical Shipping Containers; Nancy Mathis; Research, Product Development & Manufacturing, Mathis Instruments Ltd.; Nov. 5, 1999.
Validation of New Algorithm for Direct k on VIPs with TC Probe; Christina Chandler and Nancy Mathis; Mathis Instruments Ltd.; Vacuum Insulation Association Conference; Rome 2001.

* cited by examiner

Primary Examiner—Andrew H. Hirshfeild
Assistant Examiner—Lydia M. De Jesús
(74) Attorney, Agent, or Firm—Carmody & Torrance LLP

(57) ABSTRACT

The thermal conductivity of a sample of interest is measured by applying backing material to a sensor to substantially surround the sensor with the backing material and the tested material. The instrument response of the sensor corresponds to the thermal conductivity of the combination of the tested sample and the backing material. The instrument is calibrated to cancel effects of the backing material out of the instrument response.

25 Claims, 5 Drawing Sheets

DIRECT THERMAL CONDUCTIVITY MEASUREMENT TECHNIQUE

FIELD OF THE INVENTION

This invention relates to a method of measuring thermal conductivity. More specifically this invention is directed to a rapid, non-destructive technique of measuring the thermal conductivity of various materials, including solids, powders and liquids.

BACKGROUND OF THE INVENTION

Thermal conductivity measurement is a very important part of material analysis in industries ranging from electronics to construction. Materials with high conductivity for example, may be used in electronics applications as heat sinks to dissipate heat away from sensitive components. In the construction industry, low conductivity is a requirement in building materials where insulation is an important consideration.

Thermal property measurement techniques include either the transient or steady-state instrumentation categories. In steady-state measurements, heat is applied to a sample until a constant temperature equilibrium is reached, while the transient method involves applying heat to a sample over a period of time and measuring the changing temperature response of the sample. There are a number of instruments available to measure thermal conductivity using either the transient or steady-state methods. Some of these instruments include guarded hotplate, hot wire, modified hot wire, laser flash and transient plane source.

Guarded hotplate is a steady-state technique that involves placing a solid sample of fixed dimensions between two temperature controlled plates at different temperatures. Typically, one plate is heated while the other is cooled and the temperatures of the plates are monitored over time, until they reach constant temperatures ($\Delta T$). The steady-state temperature, sample thickness (L) and area (A) as well as the heat input (Q) to the system are used to calculate the thermal conductivity (k) from $Q=kA/L\Delta T$. While steady-state methods are generally very accurate, they are also time consuming, taking hours to complete a single test.

The hot wire technique is a transient method of determining thermal conductivity. This means that the temperature rise is measured during a time interval. The method involves inserting an electrically heated wire into a sample. The heat flows out radially from the wire and the temperature of the wire is measured. The plot of these temperatures versus the logarithm of time is used to calculate thermal conductivity. This technique is intrusive and therefore has limitations as to the types of materials that can be tested. (ie. powder and liquid but not solids)

Another method of measuring thermal conductivity is the transient plane source method also called the hot disk method. This is another transient technique in which the sample surrounds a heating element, but in this case, the sensor is configured as a planar circle rather than a wire or line source. The heating of the element causes a three dimensional heat flow to occur. The interface temperature is monitored and plotted against a time function, and thermal conductivity and diffusivity are calculated from an iterative curve fit to the underlying equations. This method does not require density or heat capacity information. While this method is useful for certain types of samples such as liquids or powders, the measurement of solid material requires that 2 identical sized samples of the same material be used to obtain 1 thermal conductivity measurement.

Modified hot-wire techniques also exist in the art. The modification to the basic hot wire design is that the heating element is supported on a backing material in the sensor and as such, the heat flows both into a sample to be measured and into the backing material. Since the heat flows into two different materials, the effect of the backing material must be accounted for through calibration. In order to measure thermal conductivity using a non-destructive modified transient hot wire technique, a suitable probe such as that provided for U.S. Pat. No. 5,795,064, issued Aug. 18, 1998 to Mathis, may be used, the entire disclosure of which is hereby incorporated by reference. While non-destructive due to the surface measurement and interfacial nature of the sensor interaction with the sample, they generally do not provide a direct measurement of the thermal conductivity. The primary result is effusivity ($\sqrt{(k\rho c_p)}$—the square root of thermal conductivity, density and heat capacity), requiring that the heat capacity and density parameters of the sample must be known to calculate thermal conductivity from the thermal effusivity.

Another transient technique is the laser flash diffusivity method. This method involves applying a short pulse of heat to the front face of a specimen using a laser, and measuring the temperature change of the rear face with an infrared (IR) detector. The resulting temperature rise of the rear face of the test specimen is monitored as a function of time and used, together with the sample thickness, to determine the thermal diffusivity. While this method rapidly determines diffusivity, the result must be combined with density and heat capacity data to calculate thermal conductivity.

What is needed is a rapid, non-destructive technique of measuring thermal conductivity of materials of any configuration, in which the density and heat capacity do not need to be supplied.

SUMMARY OF THE INVENTION

An object of the present invention is to provide a method and system to measure the thermal conductivity of a solid or fluid sample, rapidly and non-destructively. It is a further objective of this invention to provide a measurement technique that does not require heat capacity or density information of the sample to be known in order to determine the thermal conductivity. The present invention further provides the ability to measure both oriented materials and non-homogeneous materials.

The invention preferably involves using a modified hot wire technique to rapidly measure the thermal conductivity of a sample of interest. The disclosed method and system accomplish this by applying backing material within a sensor to support the heating element of the sensor. In this way the sensor system behaves similarly to an intrusive probe in which the sensor is completely surrounded by a material, but in this case, the material is a composite of the unknown sample and the backing material. The instrument response of the sensor corresponds to this combination of materials surrounding the heating element. The instrument is calibrated to cancel the effects of the backing material out of the instrument response.

In accordance with an aspect of the invention, there is provided a method for calibrating a sensor instrument for measuring thermal conductivity. The method comprises steps of (a) bringing a heating element supported on a backing material in contact with a known material having a known thermal conductivity such that the heating element is substantially surrounded by the known material and the backing material; (b) supplying a heat via the heating element to the combination of the backing and known material; (c) monitoring a temperature increase to obtain a raw instrument response over a predetermined time period; (d) determining, from the raw instrument response, a relation parameter indicative of the relation between the temperature increase and the time; (e) analyzing an adjusted instrument response by compensating the raw instrument response based on the relation parameter and an adjusting factor while iteratively changing the adjusting factor; (f) determining the adjusting factor as a calibration factor when the adjusted instrument response reaches predetermined agreement to the known thermal conductivity of the known material; and (g) calibrating the sensor instrument using the calibration factor.

In accordance with another aspect of the invention, there is provided a method for measuring a thermal conductivity of a material. The method comprises the steps of (1) calibrating a sensor instrument by the steps of; (a) bringing a sensor having a backing material and a heating element in contact with a known material having a known thermal conductivity such that the heating element is substantially surrounded by the known material and the backing material; (b) supplying a heat to the known material; (c) monitoring a temperature increase to obtain a raw instrument response over a predetermined time period; (d) determining, from the raw instrument response, a relation parameter indicative of the relation between the temperature increase and the time; (e) analyzing an adjusted instrument response by compensating the raw instrument response based on the relation parameter and an adjusting factor while iteratively changing the adjusting factor; and (f) determining the adjusting factor as a calibration factor when the adjusted instrument response reaches predetermined agreement to the known thermal conductivity of the known material. The method further comprises the steps of (2) bringing an unknown material to be tested in contact with the sensor such that the heating element is substantially surrounded by the unknown material and the backing material; (3) obtaining an instrument response by supplying a heat to the unknown material and monitoring a temperature increase by the sensor; and (4) obtaining the thermal conductivity of the unknown material from the instrument response based on the calibration factor.

In accordance with another aspect of the invention, there is provided a system for calibrating a sensor instrument for measuring thermal conductivity. The system comprises an instrument response receiver for receiving, from a sensor having a heating element and a backing material, a raw instrument response representing a temperature increase in a known material having a known thermal conductivity when a heat is supplied to the known material, the heating element is substantially surrounded by the known material and the backing material; a relation parameter analyzer for determining, from the raw instrument response, a relation parameter indicative of the relation between the temperature increase and the time; a calibration factor finder for analyzing an adjusted instrument response by compensating the raw instrument response based on the relation parameter and an adjusting factor while iteratively changing the adjusting factor, the instrument response analyzer determining the adjusting factor as a calibration factor when the adjusted instrument response reaches predetermined agreement to the known thermal conductivity of the known material; and a calibrator for calibrating the sensor instrument using the calibration factor.

In accordance with another aspect of the invention, there is provided an instrument for measuring thermal conductivity of a material. The instrument comprises a heating element for supplying a heat to a test material to be measured; a detector for measuring instrument responses by monitoring a temperature increase in the test material; a backing material for surrounding the heating element with the test material; and an instrument response analyzer. The instrument response analyzer has a calibration factor determiner for receiving a first instrument response when the test material is a known material having a known thermal conductivity, the calibration factor determiner further determining a relation parameter indicative of the relation between the temperature increase and the time based on the first instrument response, and analyzing an adjusted instrument response by compensating the raw instrument response based on the relation parameter and an adjusting factor while iteratively changing the adjusting factor, the instrument response analyzer determining the adjusting factor as a calibration factor when the adjusted instrument response reaches predetermined agreement to the known thermal conductivity of the known material; and a compensator for receiving a second instrument response when the test material is an unknown material having an unknown thermal conductivity, the compensator determining the thermal conductivity of the unknown material from the second instrument response based on the calibration factor.

In accordance with another aspect of the invention, there is provided a system for measuring thermal conductivity of a material. The system comprises an instrument response receiver for receiving from a sensor raw instrument responses when a heat is supplied to a test material, the sensor having a heating element and a backing material for surrounding the heating element with the test material; and an instrument response analyzer having a calibration factor determiner for receiving a first instrument response when the test material is a known material having a known thermal conductivity, the calibration factor determiner further determining a relation parameter indicative of the relation between the temperature increase and the time based on the first instrument response, and analyzing an adjusted instrument response by compensating the raw instrument response based on the relation parameter and an adjusting factor while iteratively changing the adjusting factor, the instrument response analyzer determining the adjusting factor as a calibration factor when the adjusted instrument response reaches predetermined agreement to the known thermal conductivity of the known material; and a compensator for receiving a second instrument response when the test material is an unknown material having an unknown thermal conductivity, the compensator determining the thermal conductivity of the unknown material from the second instrument response based on the calibration factor.

In accordance with another aspect of the invention, there is provided a computer readable medium storing the instructions or statements for use in the execution in a computer of the method for calibrating a sensor instrument for measuring thermal conductivity.

In accordance with another aspect of the invention, there is provided electronic signals for use in the execution in a computer of the method for calibrating a sensor instrument for measuring thermal conductivity

BRIEF DESCRIPTION OF THE DRAWINGS

The invention will be further understood from the following description with reference to the drawings in which.

Similar numerals denote similar elements throughout the drawings

DETAILED DESCRIPTION OF THE PREFERRED EMBODIMENTS

Figure 1:
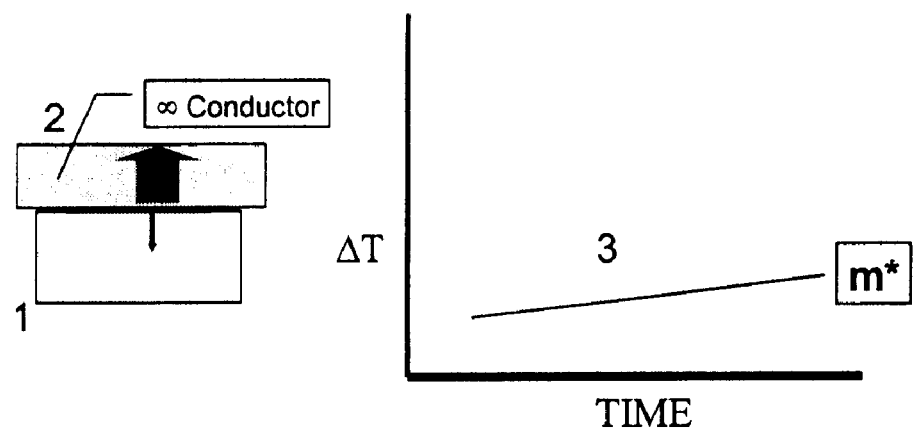
FIG. 1, graphically illustrated the sensor in contact with an infinite conductor and the linear responses (m*) of the temperature rise over time at the sensor-sample interface.

Having thus generally described the invention, reference will be made to the accompanying drawings, illustrating preferred embodiments.

The methodology disclosed herein describes a method of rapidly and non-intrusively measuring thermal conductivity of a solid or fluid. The method preferably involves using a modified hot wire sensor by applying backing material. The modified hot wire sensor has a heating element to supply heat to tested materials. The backing material is provided to support the heating element. In this way the heating element behaves in the same manner as an intrusive probe in which the heating element is completely surrounded by the sample material. However, the portion of energy that does not penetrate into the sample but rather is absorbed by the backing material must be compensated for in the instrument response. In the modified hot wire sensor, the heating element acts as a resistance thermocouple to detect temperature changes. However, the invention may be used for a different type of sensors which has a heating element and a temperature detector as separate elements. The following embodiments are described using a modified hot wire sensor, but the invention is not limited to these embodiments.

In order to clearly convey the concepts of this invention, an embodiment is described using a theoretically perfect conductor as a calibration sample material. A perfect conductor would provide infinite thermal conductivity properties. A sensor is placed in physical contact with the perfect conductor. A suitable sensor such as the TC Probe™ from Mathis Instruments could be used, however those skilled in the art will understand that other instruments could also be used in a similar manner and still remain within the scope of the invention. Heat is supplied to the sensor-sample interface by applying a constant current to the heating element. The heat can be supplied in a guarded or unguarded way to provide either one or two dimensional heat flow into the sample. Guarding reduces heat transfer at the edge of the sample and generates a pure line source heat. The sensor has a backing material, which is insulative and thus cannot absorb all of the heat applied, and the heat that is not absorbed increases the temperature at the sensor-sample interface. The effect of the backing material needs to be compensated for in the instrument response.

The temperature increase over time at the sensor-sample interface is monitored by using the heating element within the sensor. In an embodiment, the heating element of the sensor acts as a resistance thermocouple thus eliminating any bias in temperature that could exist with a secondary thermocouple. The voltage drop across the heating element increases over time as the resistance of the heating element increases. This resistance measurement is related to the temperature increase.

The data trend is analysed and fitted into an equation relating the voltage increase to a time function. In one embodiment, this can be a linear regression method in which the slope (m) of the data is determined. However, other data analysis methods can be used while remaining within the scope of the invention.

In the theoretical situation of testing a perfect conductor, only a slight temperature rise over time is received at the sensor-sample interface. This slight rise is specifically due to the insulative properties of the backing material of the sensor. An infinite conductor is a poor insulator and therefore, no heat, other than that caused by the sensor backing material is trapped at the sensor-sample interface, while a more insulative material would trap more heat at the interface resulting in a sharper increase in temperature over time.

The resulting rate of temperature rise specifically due to the heat that is not absorbed by the sensor backing is therefore referred to as the baseline. In order to operate the sensor to obtain thermal conductivity measurements, the baseline results are subtracted from the results of a sample of interest, and the corrected rate used as the instrument response. The instrument response is measured to calibrate the sensor against a plurality of thermal conductivity standards.

Figure 5:
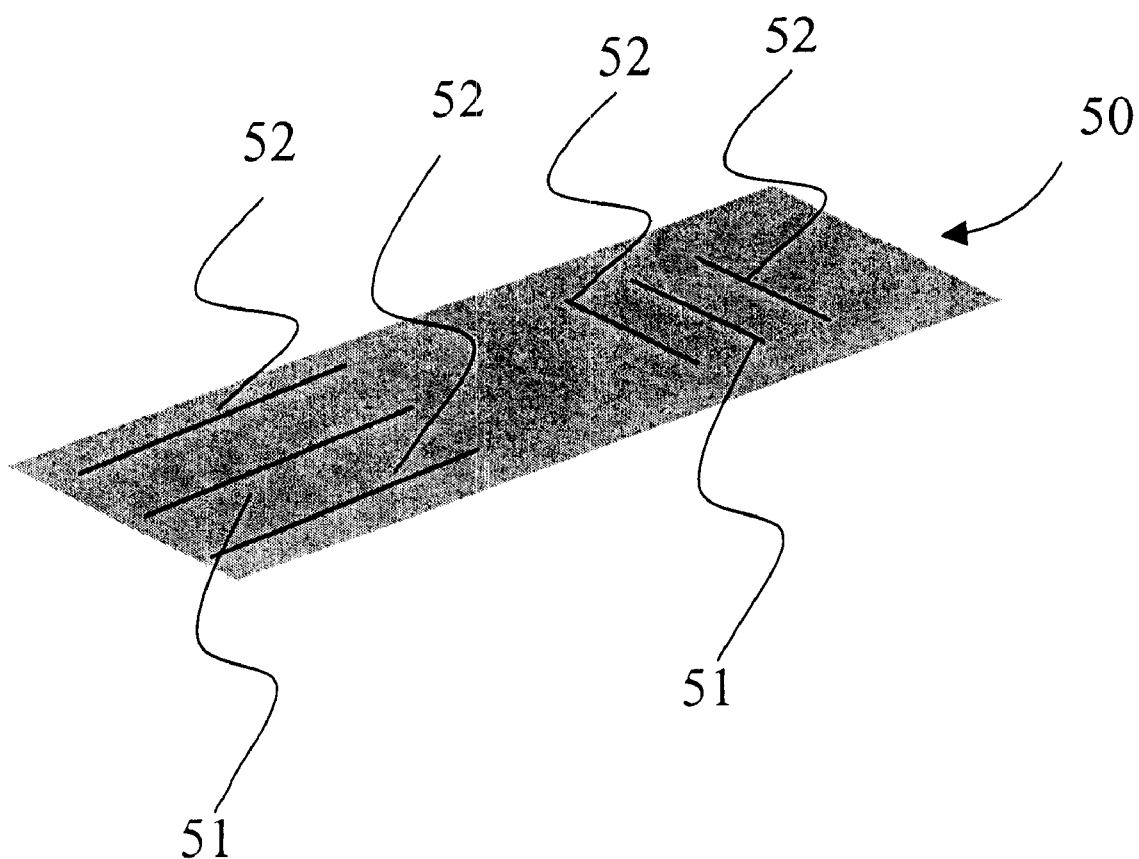
FIG. 5 is a diagram showing an example of a sensor.

FIG. 5 shows an example of a sensor 50 having a backing material 53 which may be suitably used with this invention. The sensor includes a non-electroconductive insulating body 53 shown in the example as a generally block-like structure. The body 53 may be of any suitable insulative backing material, however, an advantageous embodiment employs polyurethane foam as the non-electroconductive material. Two outer electroconductive members 52 flank a middle electroconductive member 51. The electroconductive members 51 and 52 comprise wire, ribbons etc. Any suitable form for the electroconductive members could be suitable with the proviso that the surface bearing members 51 and 52 remain reasonably flat so as not to impede contact of the sensor on the surface to be tested.

With reference to FIG. 1, a sensor 1 having a backing material is placed in thermal contact with a theoretical sample 2 of high thermal conductivity. In this embodiment, the sample 2 is an infinite conductor and the sensor 1 instrumentation is a modified hot wire.

Those skilled in the art will understand that different sample standards and different instrumentation can be used in a similar manner without departing from the scope of the invention.

A current is supplied to the resistive heating element in the sensor 1. The heat generated (resistive heat) penetrates almost instantly into the highly conductive sample 2, however, not all of the heat can be absorbed by the insulative backing material and a the portion that is not absorbed remains at the interface of the sample-sensor interface and causes an increase in temperature. This portion of non absorbed heat causes a slight temperature rise, represented by the slope (m*) 3 in FIG. 1, when measured over time. The resulting temperature rise is dependant on the insulative properties of the individual sensor and therefore can vary from device to device. This is known as the baseline effect.

Figure 2:
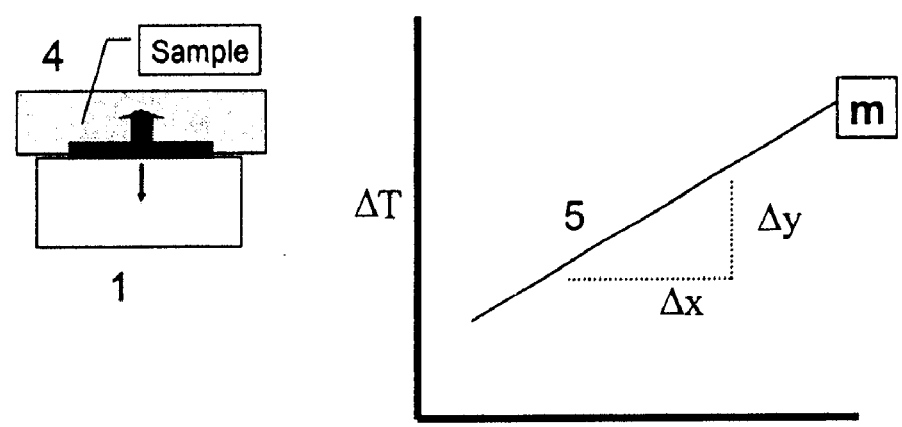
FIG. 2, graphically illustrates the sensor in contact with a sample and the linear response (m) of the temperature rise over time at the sensor-sample interface.

With reference to FIG. 2, the temperature response of a sample of interest 4 is also measured. The sample 4 is placed in thermal contact with the sensor 1, and again, heat is applied to the sample-sensor interface. Since the sample 4 is not infinitely conductive, the rate of heat transfer is lower. Some heat stays at the sensor 1 interface and causes an increase in temperature, represented by the slope (m) 5 in FIG. 2, when measured over time, where m=Δy/Δx. The slope m represents the combination of heat that did not flow into the backing or the sample. The more insulative the sample, the more heat is trapped and the higher the slope.

Figure 3:
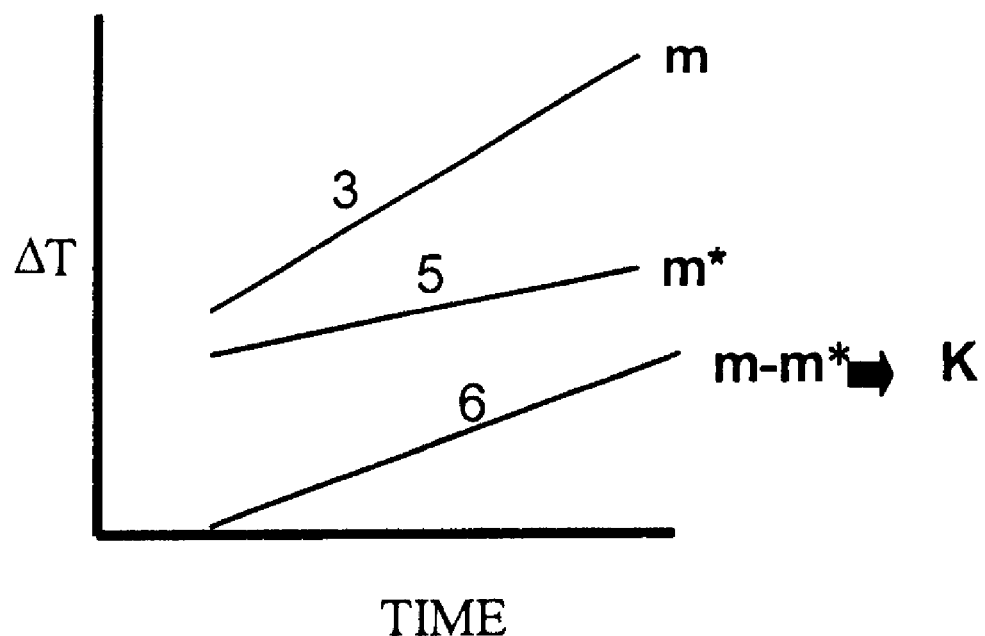
FIG. 3 graphically illustrates the difference of these slopes (m–m*) that is the instrument response that correlates to thermal conductivity.

With reference to FIG. 3, the difference of the test results is taken such that the slope response of the infinite conductor 5 is subtracted from the slope response of the sample of interest 3. The baseline temperature rise resulting from the sensor 1 backing material is cancelled out. The adjusted slope 6 is then related directly to the thermal conductivity of the sample of interest 4.

When one or more samples are tested which have established "known" thermal conductivity, the adjusted slope can be correlated to the thermal conductivity properties. The value of the calibration factor (m*) cannot be measured directly, as described in the above embodiment, since an infinite conductor is theoretical and therefore does not exist. According to the present embodiment, the value of m* is determined by iteratively changing the m* value and recalculating the correlation until it is optimized in relation to the known thermal conductivity of the sample. Future measurements on an unknown material would measure the slope m, subtract the optimized m* from the calibration and use the adjusted value in the correlation to calculate thermal conductivity.

In the embodiment of the present invention, the calibration of the sensor is carried out as follows. A material of known thermal conductivity is placed in contact with the sensor having the backing material, and heat is applied. The temperature increase over time at the sensor-sample interface is monitored by using the heating element as a resistance thermocouple. The monitored temperature provides data on the voltage drop across the sensor over time as the resistance of the heating element increases. This resistance measurement is related to the temperature increase.

The data trend is analysed and fitted into an equation which relates the voltage increase to a time function. The time function can be the square root of time or the natural logarithm of time. One or more of the equation parameters (m) is combined with a factor (m*) to compensate for heat loss to areas other than the sample. The backing material on the sensor would account for much of the compensated heat loss. The adjusted instrument response could be represented as 1/(m−m*).

The adjusted instrument response is related to the thermal conductivity (k) of the material by iteratively changing the factor (m*) until optimal agreement is reached.

Figure 4:
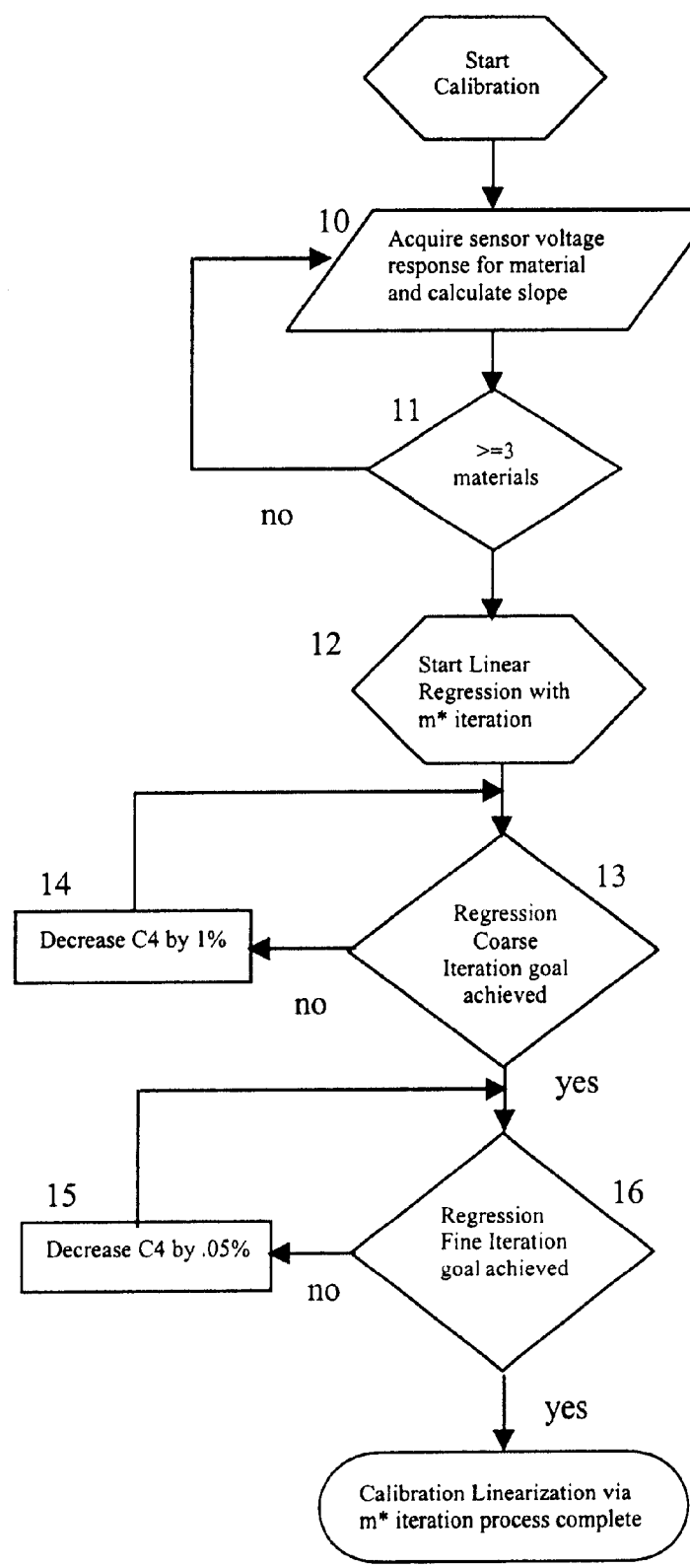
FIG. 4 is a flowchart showing a calibration process in accordance with an embodiment of the invention.

A further explanation of the embodiment of the invention is disclosed as a system flow chart in FIG. 4. In this embodiment, the calibration may be carried out by two steps: a coarse iteration process and then a fine iteration process. In the first box 10 the sensor voltage response for a known material is obtained and the slope (m) calculated. This raw data represents the temperature response of the material with known thermal conductivity when heat is applied to the sensor-sample interface. The measurement and calculation of the slope (m) is repeated until a predetermined number of known materials are measured 11. In this embodiment, the predetermined number is shown as "3", but this may be varied depending on the accuracy required for the sensor.

Once the predetermined number of m values are obtained, linear regression is started using iteration of a factor m* 12. The factor m* is a function of a variable. When a constant voltage Vo is applied to the heating element, the factor m* may be expressed such as:

$$m^* = C_4 \times Vo$$

wherein $C_4$ is a variable. The factor m* is the calibration factor needed to optimize the instrument response.

First, course regression is carried out until a preset coarse regression goal is achieved 13. During each iteration, the variable for m* is decreased by a preset amount, e.g., $C_4$ is decreased by 1% 14. Once the coarse iteration goal is achieved 13, fine regression is carried out until a preset fine regression goal is achieved 16. During each iteration, the variable for m* is decreased by a preset amount, e.g., $C_4$ is decreased by 1% 15. When the goal is achieved, the resultant factor m* is determined as the calibration factor. The sensor is calibrated using m* such that the output slope value m automatically represents a value in which the baseline is subtracted (m−m*).

These processes may be expressed by solving the following equation:

$$y_{new} = (k \times M) + Y_o$$

wherein $y_{new}$ is the new value of the regression equation; and $Y_o$ is a constant. Solving for k leads to the following sets of equations:

$$V_o/(m-m^*) = (k \times M) + Y_o$$

where $k = (1/M)(V_o/(m-m^*)) - (Y_o/M)$
then $k = (1/M)(V_o/(m-(C_4 \times Vo))) - (Y_o/M)$
then $k = (1/M)(1/(m/V_o) - C_4)) - (Y_o/M)$
letting $M = 1/C_2$ and $Y_o = -(C_3 \times M)$
we get $k = C_2/(m/Vo - C_4) + C_3$ Accordingly, when a test material having an unknown thermal conductivity k is measured by thus calibrated sensor, the thermal conductivity k is calculated as follows:

$$k = C_2/(m/Vo - C_4) + C_3$$

This embodiment can rapidly determine thermal conductivity up to 15 W/m·K, without requiring density or heat capacity values. The measurement may be completed in a short time period, e.g., in the order of seconds or minutes.

Further, this new technique can be applied to a plurality of different materials including solids, powders and fluids. Also, it further allows the measurement of materials that are non-homogenous. In an embodiment, materials are tested with packaging or within a container. Unwanted data from materials encasing a material of interest can be blanked out of the final results. This unwanted data would include thermal information from packaging or insulating materials. In the case of a liquid, the containment material would be plastic or glass bottles or dishes. Taking into account, the baseline effect from the sensor backing, this measurement can be performed by calibrating the sensor with the container between the sensor and the calibration materials. In that way the instrument response is correlated to the physical property of the material on the other side of a container.

In another embodiment of the invention, the methodology described enables the measurement of a sample of interest enclosed in containment materials, wherein the goal is to compensate for the portion of the thermal conductivity attributed to the containment material. The containment material encasing a sample of interest can be measured separately from the combined measurement of the sample of interest with the containment material.

Using the technique described above, the temperature response of the containment material alone can be blanked out of the temperature response of the sample of interest with the containment material. The resulting slope is then related directly to the thermal conductivity of the sample of interest effectively compensating for the effects of the encasing material.

Using the sensor described in FIG. 5, with the electro-conductive members 51 and 52, in a first possible testing procedure, the outer strips 52 may be heated to provide thermal guarding therefore reducing heat flow in the direction of these members. This feature provides a one-dimensional heat flow when the guard members 52 are activated, and a two-dimensional test when they are not activated. The slope of the graph of the sensor data differs between the one-dimensional and the two-dimensional test. In the one-dimensional test the slope is defined by the following equation:

$$m=dv/d(\operatorname{sqrt}(t)) \text{ (volts/(sqrt(sec))}$$

whereas for the two-dimensional test the slope is defined by the following equation:

$$m=dv/d(\ln(t)) \text{ (volts/(ln(sec))}$$

Figure 6:
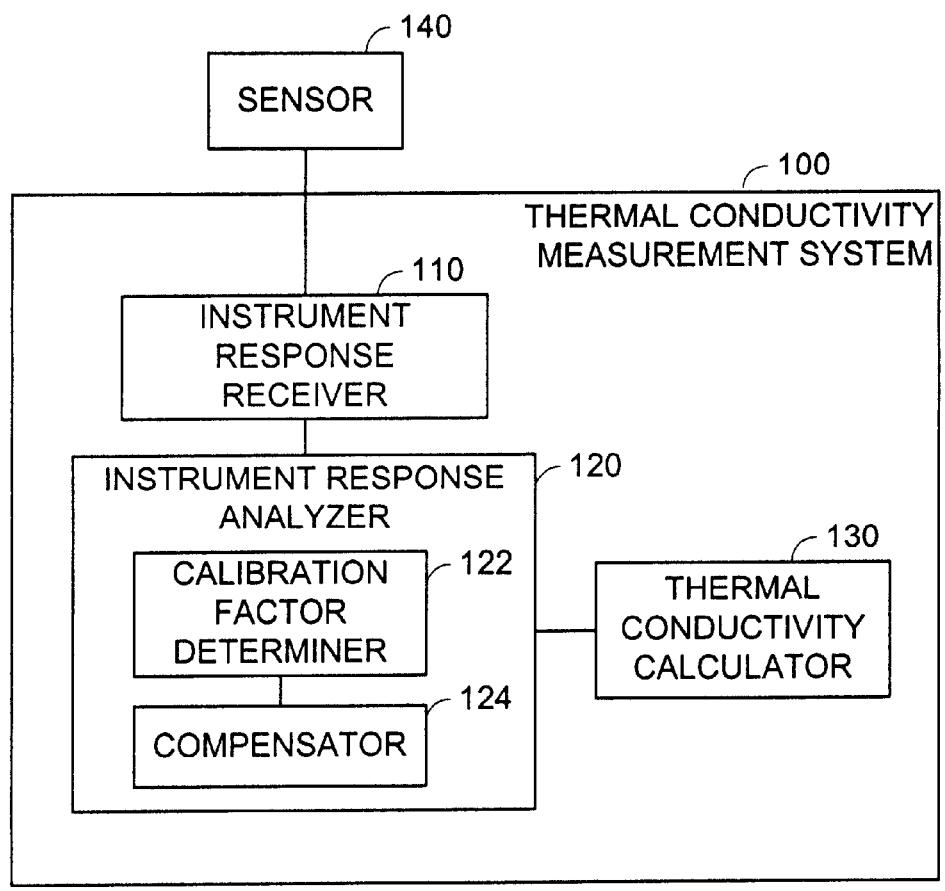
FIG. 6 is a block diagram showing a thermal conductivity measurement system in accordance with an embodiment of the invention.

FIG. 6 shows a system for measuring thermal conductivity in accordance with an embodiment of the invention. The system 100 comprises an instrument response receiver 110, an instrument response analyzer 120 and a thermal conductivity calculator 130.

The instrument response receiver 110 receives instrument responses from a sensor having a backing material 140. The instrument response analyzer 120 analyzes the received instrument responses. The thermal conductivity calculator 130 calculates thermal conductivities based on the output of the analyzer 120.

The instrument response analyzer 120 has a calibration factor determiner 122 for determining a calibration factor, and a compensator 124 for calibrating the sensor to compensate instrument responses by the calibration factor.

Figure 7:
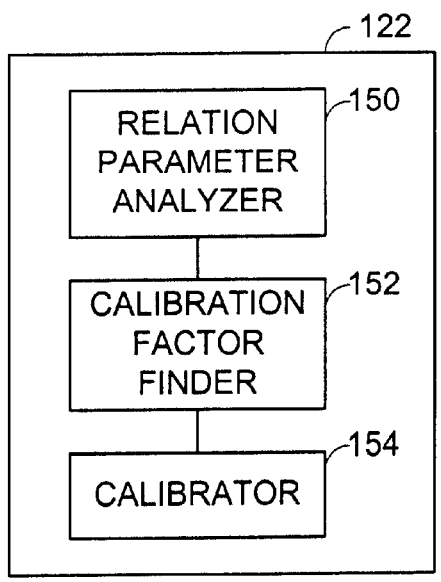
FIG. 7 is a block diagram showing an example of the calibration system.

As shown in FIG. 7, the calibration factor determiner 122 may comprise a relation parameter analyzer 150, a calibration factor finder 152 and a calibrator 154. When a material having a known thermal conductivity, the instrument response of the material received by the receiver 110 is fed to the relation parameter analyzer 150. From the instrument response, the relation parameter analyzer 150 determines a relation parameter indicative of the relation between the temperature increase and the time.

The calibration factor finder 152 analyzes an adjusted instrument response by compensating the received instrument response based on the relation parameter and an adjusting factor while iteratively changing the adjusting factor. The instrument response analyzer 152 determines the adjusting factor as a calibration factor when the adjusted instrument response reaches predetermined agreement to the known thermal conductivity of the known material. The calibrator 154 calibrates the instrument 100 using the calibration factor.

For example, in the embodiment described referring to FIG. 4, the relation parameter analyzer 150 determines a slope m as the relation parameter. The calibration factor finder 152 uses linear regression to find a calibration factor m*, as described above.

The thermal conductivity measurement system of the present invention may be implemented by any hardware, software or a combination of hardware and software having the above described functions. The software code, either in its entirety or a part thereof, may be stored in a computer readable memory. Further, a computer data signal representing the software code, which may be embedded in a carrier wave, may be transmitted via a communication network. Such a computer readable memory and a computer data signal are also within the scope of the present invention, as well as the hardware, software and the combination thereof.

Although the embodiments of the invention have been described above, it is not limited thereto and it will be apparent to those skilled in the art of numerous modifications form part of the present invention insofar as they do not depart from the scope of the invention as defined in the claims.

We claim:

1. A method for calibrating a sensor instrument for measuring thermal conductivity; the method comprising steps of:
   (a) bringing a heating element supported on a backing material in contact with a known material having a known thermal conductivity such that the heating element is substantially surrounded by the known material and the backing material;
   (b) supplying a heat via the heating element to the combination of the backing and known material;
   (c) monitoring a temperature increase to obtain a raw instrument response over a predetermined time period;
   (d) determining, from the raw instrument response, a relation parameter indicative of the relation between the temperature increase and the time;
   (e) analyzing an adjusted instrument response by compensating the raw instrument response based on the relation parameter and an adjusting factor while iteratively changing the adjusting factor;
   (f) determining the adjusting factor as a calibration factor when the adjusted instrument response reaches predetermined agreement to the known thermal conductivity of the known material; and
   (g) calibrating the sensor instrument using the calibration factor.

2. The method as claimed in claim 1 wherein step (b) supplies the heat by the heating element acting as a resistance thermocouple.

3. The method as claimed in claim 1 wherein step (b) supplies a constant current to the heating element.

4. The method as claimed in claim 1 wherein step (c) monitors the temperature increase in the heating element.

5. The method as claimed in claim 4 wherein step (c) monitors the temperature increase as voltage changes across the heating element.

6. The method as claimed in claim 1 wherein step (c) monitors the temperature increase at an interface between the known material and the sensor instrument.

7. The method as claimed in claim 1 wherein step (d) determines the relation parameter by performing regression analysis on the raw instrument response.

8. The method as claimed in claim 7 wherein step (d) determines the relation parameter by a linear regression, and a resultant slope value is determined as the relation parameter.

9. The method as claimed in claim 8 wherein step (e) compensates the raw instrument response by subtracting the adjusting factor from the slope value.

10. The method as claimed in claim 1 wherein step (e) comprises steps of performing coarse regression analysis by coarsely changing the adjusting factor until the adjusted instrument response reaches preset coarse agreement to the known thermal conductivity, and further performing fine regression analysis by finely changing the adjusting factor.

11. The method as claimed in claim 1 further comprising a step of repeating step (a) through step (d) for one or more different known materials, each having a different known thermal conductivity; and wherein step (e) determines the adjusted instrument response using multiple adjusting factors obtained for multiple known materials.

12. The method as claimed in claim 1 wherein the predetermined time period is in the order of seconds.

13. The method as claimed in claim 1 wherein step (a) brings the heating element in contact with a known material through a container that is used for measuring a material for which a thermal conductivity is to be measured, such that the backing material and the container surround the heating element.

14. The method as claimed in claim 1 wherein step (g) compensates the instrument response for heat loss to the backing material using the calibration factor.

15. A method for measuring a thermal conductivity of a material, the method comprising the steps of:
  (1) calibrating a sensor instrument by the steps of;
    (a) bringing a sensor having a backing material and a heating element in contact with a known material having a known thermal conductivity such that the heating element is substantially surrounded by the known material and the backing material;
    (b) supplying a heat to the known material;
    (c) monitoring a temperature increase to obtain a raw instrument response over a predetermined time period;
    (d) determining, from the raw instrument response, a relation parameter indicative of the relation between the temperature increase and the time;
    (e) analyzing an adjusted instrument response by compensating the raw instrument response based on the relation parameter and an adjusting factor while iteratively changing the adjusting factor; and
    (f) determining the adjusting factor as a calibration factor when the adjusted instrument response reaches predetermined agreement to the known thermal conductivity of the known material;
  (2) bringing an unknown material to be tested in contact with the sensor such that the heating element is substantially surrounded by the unknown material and the backing material;
  (3) obtaining an instrument response by supplying a heat to the unknown material and monitoring a temperature increase by the sensor; and
  (4) obtaining the thermal conductivity of the unknown material from the instrument response based on the calibration factor.

16. The method as claimed in claim 15 wherein step (1) calibrates the sensor instrument with a container; and step (2) brings the unknown material in contact with the sensor through the container.

17. A system for calibrating a sensor instrument for measuring thermal conductivity; the system comprising:
  an instrument response receiver for receiving, from a sensor having a heating element and a backing material, a raw instrument response representing a temperature increase in a known material having a known thermal conductivity when a heat is supplied to the known material, the heating element is substantially surrounded by the known material and the backing material;
  a relation parameter analyzer for determining, from the raw instrument response, a relation parameter indicative of the relation between the temperature increase and the time;
  a calibration factor finder for analyzing an adjusted instrument response by compensating the raw instrument response based on the relation parameter and an adjusting factor while iteratively changing the adjusting factor, the instrument response analyzer determining the adjusting factor as a calibration factor when the adjusted instrument response reaches predetermined agreement to the known thermal conductivity of the known material; and
  a calibrator for calibrating the sensor instrument using the calibration factor.

18. The system as claimed in claim 17 wherein the relation parameter analyzer is a regression analyzer.

19. The system as claimed in claim 18 wherein the relation parameter analyzer is a linear regression analyzer.

20. The system as claimed in claim 17 wherein the instrument response analyzer determines the adjusted instrument response using multiple adjusting factors obtained for multiple known materials having various known thermal conductivities.

21. An instrument for measuring thermal conductivity of a material; the instrument comprising:
  a heating element for supplying a heat to a test material to be measured;
  a detector for measuring instrument responses by monitoring a temperature increase in the test material;
  a backing material for surrounding the heating element with the test material; and
  an instrument response analyzer having:
    a calibration factor determiner for receiving a first instrument response when the test material is a known material having a known thermal conductivity, the calibration factor determiner further determining a relation parameter indicative of the relation between the temperature increase and the time based on the first instrument response, and analyzing an adjusted instrument response by compensating the raw instrument response based on the relation parameter and an adjusting factor while iteratively changing the adjusting factor, the instrument response analyzer determining the adjusting factor as a calibration factor when the adjusted instrument response reaches predetermined agreement to the known thermal conductivity of the known material; and
    a compensator for receiving a second instrument response when the test material is an unknown material having an unknown thermal conductivity, the compensator determining the thermal conductivity of the unknown material from the second instrument response based on the calibration factor.

22. The instrument as claimed in claim 21 wherein the detector is a resistance thermocouple acting as the heating element.

23. The instrument as claimed in claim 22 wherein the detector monitors voltage changes across the heating element.

24. A system for measuring thermal conductivity of a material; the system comprising:

an instrument response receiver for receiving from a sensor raw instrument responses when a heat is supplied to a test material, the sensor having a heating element and a backing material for surrounding the heating element with the test material; and an instrument response analyzer having:
  a calibration factor determiner for receiving a first instrument response when the test material is a known material having a known thermal conductivity, the calibration factor determiner further determining a relation parameter indicative of the relation between the temperature increase and the time based on the first instrument response, and analyzing an adjusted instrument response by compensating the raw instrument response based on the relation parameter and an adjusting factor while iteratively changing the adjusting factor, the instrument response analyzer determining the adjusting factor as a calibration factor when the adjusted instrument response reaches predetermined agreement to the known thermal conductivity of the known material; and a compensator for receiving a second instrument response when the test material is an unknown material having an unknown thermal conductivity, the compensator determining the thermal conductivity of the unknown material from the second instrument response based on the calibration factor.

25. The system as claimed in claim 24 further comprising a thermal conductivity calculator for calculating the thermal conductivity of the test unknown material based on the output of the compensator using the thermal conductivity of the known material.

* * * * *

UNITED STATES PATENT AND TRADEMARK OFFICE
CERTIFICATE OF CORRECTION

PATENT NO.   : 6,676,287 B1
DATED        : January 13, 2004
INVENTOR(S)  : Nancy Mathis et al.

It is certified that error appears in the above-identified patent and that said Letters Patent is hereby corrected as shown below:

<u>Title page,</u>
Item [75], should read:
-- [75] Inventors:    Nancy Mathis, Fredericton, NB, Canada
                      Christina Chandler, San Jose, CA (US) --
Item [73], should read:
-- [73] Assignee:     Mathis Instruments, Ltd., Fredericton, NB, Canada --

Signed and Sealed this

Fourth Day of May, 2004

JON W. DUDAS
*Acting Director of the United States Patent and Trademark Office*